US011850139B2

(12) United States Patent
Scheeff et al.

(10) Patent No.: US 11,850,139 B2
(45) Date of Patent: *Dec. 26, 2023

(54) EMBOLIC PROTECTION BASKET APPARATUS

(71) Applicant: C.R. BARD, INC., Murray Hill, NJ (US)

(72) Inventors: Mark Christopher Scheeff, San Francisco, CA (US); Anant V. Hegde, Hayward, CA (US)

(73) Assignee: C.R. BARD, INC., Murray Hill, NJ (US)

( * ) Notice: Subject to any disclaimer, the term of this patent is extended or adjusted under 35 U.S.C. 154(b) by 334 days.

This patent is subject to a terminal disclaimer.

(21) Appl. No.: 17/231,759

(22) Filed: Apr. 15, 2021

(65) Prior Publication Data

US 2021/0228328 A1 Jul. 29, 2021

Related U.S. Application Data

(63) Continuation of application No. 16/082,119, filed as application No. PCT/US2017/020452 on Mar. 2, 2017, now Pat. No. 11,007,045.

(Continued)

(51) Int. Cl.
*A61F 2/01* (2006.01)
*A61F 2/24* (2006.01)

(52) U.S. Cl.
CPC ............ *A61F 2/0108* (2020.05); *A61F 2/013* (2013.01); *A61F 2/2433* (2013.01); *A61F 2002/018* (2013.01); *A61F 2250/001* (2013.01)

(58) Field of Classification Search
CPC ............ A61B 17/12109; A61B 17/221; A61B 2017/2212; A61F 2/01; A61F 2/013;

(Continued)

(56) References Cited

U.S. PATENT DOCUMENTS

| 7,780,696 B2 | 8/2010 | Daniel et al. |
| 8,974,490 B2 | 3/2015 | Jonsson |

(Continued)

FOREIGN PATENT DOCUMENTS

| CN | 1278713 | 1/2001 |
| FR | 2831422 | 5/2003 |

(Continued)

OTHER PUBLICATIONS

Notification of Transmittal of the International Search Report, the Search Report, and the Written Opinion of the International Searching Authority for International App. No. PCT/US17/20452, dated Jun. 21, 2017.

(Continued)

*Primary Examiner* — Ashley L Fishback
(74) *Attorney, Agent, or Firm* — Garvey, Smith & Nehrbass, Patent Attorneys, L.L.C.; Charles C. Garvey, Jr.; Fabian M. Nehrbass

(57) ABSTRACT

The present invention provides an aortic embolic filter mounted on a catheter. A pair of spaced apart hubs are provided, one hub being a catheter hub mounted on the catheter, the other hub being a tip hub spaced distally of the catheter hub. A filter basket is attached to the hubs and positioned distally of the catheter hub. The basket includes multiple supports that each span the two hubs. A filter material/sheet is supported by the supports, the filter material having concave and convex surfaces, first and second edge portions, and an opening that spans most of the distance between the hubs and in between the filter material edge portions. One of the supports is movable relative to the catheter hub. An operator, controller or handle enables the movable support to change length between the hubs to put more or less of a curvature of the filter basket.

20 Claims, 14 Drawing Sheets

Related U.S. Application Data

(60) Provisional application No. 62/302,491, filed on Mar. 2, 2016.

(58) Field of Classification Search
CPC .......... A61F 2002/011; A61F 2002/016; A61F 2002/018
See application file for complete search history.

(56) References Cited

U.S. PATENT DOCUMENTS

| | | |
|---|---|---|
| 2004/0111111 A1 | 6/2004 | Lin |
| 2005/0090858 A1 | 4/2005 | Pavlovic |
| 2006/0155305 A1 | 7/2006 | Freudenthal et al. |
| 2010/0146922 A1 | 6/2010 | Greenwood |
| 2013/0123835 A1 | 5/2013 | Anderson et al. |
| 2013/0144326 A1 | 6/2013 | Brady et al. |
| 2014/0074151 A1 | 3/2014 | Tischler et al. |
| 2014/0172006 A1 | 6/2014 | Stack et al. |
| 2014/0243881 A1 | 8/2014 | Lees et al. |
| 2014/0249566 A1 | 9/2014 | Quinn et al. |
| 2014/0276922 A1 | 9/2014 | McLain et al. |
| 2014/0350523 A1 | 11/2014 | Dehdashtian et al. |
| 2014/0371781 A1 | 12/2014 | Morgan |
| 2015/0150672 A1 | 6/2015 | Ma |
| 2015/0313701 A1 | 11/2015 | Krahbichler |

FOREIGN PATENT DOCUMENTS

| | | |
|---|---|---|
| WO | 2004019817 | 3/2004 |
| WO | 2012009558 | 1/2012 |
| WO | 2014199381 | 12/2014 |
| WO | 2015/055605 | 4/2015 |
| WO | 2015/104645 | 7/2015 |
| WO | 2015104656 | 7/2015 |

OTHER PUBLICATIONS

Extended European Search Report, dated Jan. 8, 2020, The Hague (5 pages).

EMBOLIC PROTECTION BASKET APPARATUS

CROSS-REFERENCE TO RELATED APPLICATIONS

This application is a continuation of U.S. patent application Ser. No. 16/082,119, filed Sep. 4, 2018, now U.S. Pat. No. 11,007,045, which is a 35 U.S.C. § 371 National Stage Entry application of International Patent Application Serial No. PCT/US2017/020452, filed Mar. 2, 2017, which claims the benefit of U.S. Provisional Patent Application Ser. No. 62/302,491, filed 2 Mar. 2016. Priority of U.S. Provisional Patent Application Ser. No. 62/302,491, filed 2 Mar. 2016, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to an improved embolic protection catheter/basket apparatus for use during heart valve replacement and related procedures.

2. General Background of the Invention

In recent years, aortic valve replacement has been achieved through a minimally invasive surgical procedure called transcatheter aortic valve replacement (TAVR) or transcatheter aortic valve implantation (TAVI). TAVR provides a new valve without removing the old, damaged valve. Instead, a stent-like valve is crimped onto a balloon, passed through the femoral artery, the aorta, and finally into position within the aortic valve annulus. The balloon is expanded inside the native valve to place the prosthetic valve over the native aortic valve. The new valve pushes the old valve leaflets out of the way, and the tissue in the replacement valve takes over the job of regulating blood flow. This procedure is also done with self expanding prosthetic valves, without a balloon.

Additional left side, catheter based heart procedures, such as coronary angiography, percutaneous coronary intervention (PCI), mitraclip and atrial fibrillation (afib) ablation procedures are routinely done. Finally, surgical procedures such as coronary artery bypass graft (CABG) and surgical aortic valve replacement are routinely performed.

The above discussed procedures can create/dislodge emboli that can travel to other parts of the body, in particular, the brain. Emboli lodging in the brain can create many effects such as infarctions visible on the MRI but with no obvious clinical manifestation ("silent lesions"), minor cognitive impairment or major cognitive impairment, such as stroke. Effects may be transient or permanent.

Patents have issued that relate generally to embolic filters. The following table lists possibly relevant examples. The order of listing in the table is of no significance.

| U.S. Pat. No./ Publication No. | Title | Issue Date MM-DD-YYYY |
| --- | --- | --- |
| 7,780,696 | Distal Protection Device and Method | Aug. 24, 2010 |
| 2005/0090858 | Distal Protection Device with Electrospun Polymer Fiber Matrix | Apr. 28, 2005 |
| 2006/0155305 | Extraction Device | Jul. 13, 2006 |
| 2014/0074151 | Fixation Anchor Design for an Occlusion Device | Mar. 13, 2014 |
| 2014/0276922 | Shape Memory Metal Emboli Trap | Sep. 18, 2014 |
| 2014/0350523 | Aortic Occlusion Device | Nov. 27, 2014 |
| 2014/0371781 | Covered Filter Catheter Apparatus and Method of Using Same | Dec. 18, 2014 |
| 2015/0150672 | Embolus Removal Device with Blood Flow Restriction and Related Methods | Jun. 4, 2015 |

BRIEF SUMMARY OF THE INVENTION

One way to mitigate these prior art problems is to provide a device that preferably captures or deflects particles that would otherwise end up in the brain. The apparatus of the present invention solves the problems confronted in the art in a simple and straightforward manner: a sheath, (e.g., a 5 F to 16 F sheath, preferably a 6 F to 14 F sheath, and most preferably a 7 F to 10 F sheath) is placed in the aorta through the femoral access over a guidewire, preferably one with a diameter of 0.009-0.045 inches (0.023-0.114 cm), more preferably with a diameter of 0.014-0.035 inches (0.036-0.0889 cm), and most preferably with a diameter of 0.035 inches (0.0889 cm). The embolic protective basket/catheter apparatus of the present invention is then introduced into the sheath and over the guidewire, tracked over the wire to the aortic arch region while the user views the position under fluoroscopy. This basket or filter and catheter has a basket with fixed and movable (adjustable) supports or arms to which a sheet of filter material attaches. The filter material or sheet attaches to multiple fixed supports or arms. A movable or adjustable arm is preferably not attached to the filter material, but can be used to change its shape or configuration.

Operating a "slider" or actuator on top of a controller or handle deploys the basket, pulling the sheath and placing the basket/filter in a desired location. Orientation of the filter/basket position can be manipulated by rotating the catheter shaft while the adjustable support arm is under minimum tension. Once the orientation of the filter position is achieved, rotating a tension knob on the controller or handle increases the movable support arm tension. This increased tension on the movable support arm will help in keeping the filter in position during the procedure. For instance, increasing the tension on the movable support causes the filter to form an arc that closely matches the aortic arch curve. A pigtail catheter can be advanced over the guidewire. The pigtail catheter is then preferably placed in the left ventricular outflow tract (LVOT) or wherever desired. The pigtail catheter is preferably used to measure/monitor cardiac output during the procedure. The transcatheter aortic valve implantation or TAVI procedure can then be completed through a second femoral access created in the patient. In order to remove the basket and catheter, the "slider" is then advanced to advance the sheath over the basket thus collapsing the basket. The entire basket/catheter apparatus is then pulled out preferably using the femoral access sheath.

The basket/catheter apparatus has a basket or filter preferably at the distal end, a controller or handle preferably at the proximal end and a flexible polymeric catheter or catheter shaft preferably connecting the two ends.

The basket (or filter) can preferably be constructed out of a plurality of fixed (not adjustable) shape set ribbons (e.g., nitinol) and a movable or adjustable wire. In one embodiment, the basket/filter can have at least four of the ribbons, wires, arms or supports. Preferably, three supports or arms are fixed at both ends. In a preferred embodiment, one of the supports or arms is fixed only at the distal end, while sliding at its other end allowing for basket size adjustments appropriately to the anatomy/procedure.

The fixed nitinol supports or arms are shape-set in the configuration out of preferably 0.002-0.010 inches (0.005-0.025 cm) by 0.010-0.060 inches (0.025-0.152 cm), more preferably 0.003-0.007 inches (0.008-0.018 cm) by 0.030-0.050 inches (0.076-0.127 cm), and most preferably 0.005 inches by 0.020 inches (0.0127 cm by 0.0508 cm) nitinol support or ribbon. The adjustable support or arm is preferably fixed only at the distal end and is shape-set out of preferably 0.005-0.040 inch (0.0127-0.102 cm) diameter wire, more preferably 0.010-0.030 inch (0.025-0.076 cm) diameter wire, and most preferably, 0.02 inch (0.0508 cm) diameter wire. All four supports or arms are preferably secured at the distal end using a fitting, hub or tip made out of e.g., polymeric material or metal. The nitinol supports or arms can be secured to a fitting, hub or tip either by e.g., adhesive, welding, soldering or crimping. The tip, fitting or hub has a through hole in the middle for receiving a guidewire, preferably one with a diameter of 0.009-0.045 inches (0.023-0.114 cm), more preferably with a diameter of 0.014-0.035 inches (0.0356-0.0889 cm), and most preferably with a diameter of about 0.035 inches (0.0889 cm), to pass through for the initial placement of the basket/filter in the aorta.

A filter material is preferably secured to the three fixed filter supporting arms by e.g., sewing, adhesives or by heat-sealing to itself. The filter material can be made out of nylon fabric with a thickness of preferably 5-200 µm, more preferably 25-150 µm, and most preferably around 84 µm, and having a mesh opening of preferably 10-200 µm, more preferably 50-175 µm, and most preferably 140 µm. The nitinol arms or fixed supports are preferably assembled with the filter material to form a minimum deployed diameter of about 0.075 inches (0.1905 cm). The proximal end of the basket is preferably assembled using a hub, fitting or sprocket that is similarly configured to the distal hub with the exception that the movable or adjustable supporting arm securement hole is preferably large enough for the movable/adjustable arm to slide freely.

The fixed filter supporting arms are preferably secured at the proximal end in similar fashion as at the tip, and these three arms are terminated at this junction. The movable or adjustable supporting arm is passed through the sprocket and terminated in the controller or handle of the catheter. In order to better secure the filter material and to make it collapse easily, small diameter wires can be weaved through the filter material like "ribs". The ends of the ribs can be secured to the fixed filter supporting arms either using e.g., adhesive, solder or welds. The super-elastic nitinol wires that can be used for ribs can be preferably 0.001-0.010 inches (0.00254-0.0254 cm) in diameter, more preferably 0.002-0.008 inches (0.00508-0.02032 cm) in diameter, and most preferably 0.003 inches (0.00762 cm) in diameter. The number and spacing of ribs can vary. Typical spacing between the ribs can be preferably 0.050-0.500 inches (0.127-1.270 cm), more preferably 0.100-0.300 inches (0.254-0.762 cm), and most preferably 0.200 inches (0.508 cm).

The basket or filter is preferably secured to a polymeric shaft by e.g., heat fusing or by adhesives. A typical cross sectional view of the catheter assembly is shown in FIG. 18. The catheter shaft can be, for example, an extruded polymeric tube having a bore or lumen. The polymeric shaft can preferably be reinforced with e.g., metal braids, monofilament or yarn to improve column strength and to improve kink resistance. Polymeric material that can be used for the shaft can be e.g., Pebax, Nylon, Polyvinylidene fluoride (PVDF) or Polyurethane.

The catheter shaft connects to a controller or handle preferably at the proximal end via a strain relief. The controller or handle preferably has a slider for deploying and collapsing the basket. The movable or adjustable supporting arm is preferably attached to the rotating knob in the handle. Rotation of the knob in clockwise direction will preferably increase the size of the basket, thus keeping the filter in close contact with the aorta wall. The controller or handle preferably has a flush port on top that allows for flushing the catheter lumen with e.g., saline, heparin, contrast or other media. The guidewire/pigtail port allows for the guidewire/pigtail changes. The handle and parts of the handle can be molded out of e.g., Acrylonitrile butadiene styrene (ABS), Polycarbonate, Polystyrene, Nylon, Polybutylene terephthalate (PBT), Polyurethane or Acrylic plastic material. The strain relief can be a soft flexible molded part of e.g., Pebax, Polyurethane, Santoprene or other thermoplastic elastomers (TPEs).

The present invention can be sheath compatible, preferably a 5 F-16 F sheath, more preferably a 6 F-14 F sheath, and most preferably, a 9 F sheath, and has the ability to deliver over a guidewire, preferably one with a diameter of 0.009-0.045 inches (0.023-0.114 cm), more preferably with a diameter of 0.014-0.035 inches (0.0356-0.0889 cm), and most preferably with a diameter of 0.035 inches (0.0889 cm). A sheath lumen doubles as the port for a pigtail catheter, preferably a 3 F-10 F, more preferably 4 F-9 F, and most preferably, a 5 F-8 F (e.g., 5 F to 6 F).

The basket portion is preferably able to filter emboli of at least 140 microns. The apparatus has the ability to reposition and can be visible under fluoroscope.

The apparatus has the ability to track TAVR catheter while in place. It includes an easy to use handle or controller preferably with a flush port and has the ability to be retrieved back into a sheath, preferably a 5 F-16 F sheath, more preferably a 6 F-14 F sheath, and most preferably, a 9 F sheath.

The filter/basket can be coated with e.g., heparin or other agents.

The basket like structure with the filter can be deployed in the aorta prior to a selected heart procedure. The basket can be positioned in the aorta such that the filter is preferably aligned to filter out the blood flow that enters the brain through the brachiocephalic artery, carotid artery and left subclavian artery (see FIG. 1).

The present invention thus provides an aortic embolic filter/catheter apparatus with an elongated catheter having a length, proximal and distal end portions and a catheter lumen with a catheter central, longitudinal axis.

A pair of spaced apart fittings or hubs are provided, preferably with at least one fitting or hub being a catheter hub or sprocket mounted on the catheter, the other fitting or hub preferably being a tip hub spaced distally of the catheter hub.

A filter basket is preferably attached to the hubs and positioned distally of the catheter hub.

The filter basket preferably includes multiple supports that each span from the catheter hub to the tip hub. Some of these supports are fixed. One of the supports is preferably movable/adjustable relative to the catheter hub or sprocket. The filter/basket preferably has a convex side that is preferably aligned with the arteries that discharge blood from the aorta. The filter or basket preferably has a concave side or concavity opening, socket or receptacle that receives and holds emboli thus trapping same before they can reach the patient's brain.

A filter material or filter sheet is preferably supported by the supports, the filter material so supported having concave and convex surfaces, first and second edge portions, and an opening, concavity, socket or receptacles that spans most of the distance between the hubs.

One of the supports preferably is a support that is movable relative to the catheter hub.

An operator, controller or handle preferably enables the movable support to change length between the hubs to put more or less of a curvature to the filter basket.

In one embodiment, the fixed supports are preferably curved.

In one embodiment, there are preferably at least three fixed supports.

In one embodiment, the movable support preferably extends the full length of the catheter.

In one embodiment, the apparatus preferably includes a guidewire, each of the hubs preferably having a hub opening and the guidewire preferably extending through the hub openings.

In one embodiment, the controller is preferably attached to the proximal end portion of the catheter, the controller preferably moving the movable support.

In one embodiment, the controller preferably includes a rotatable knob.

In one embodiment, each hub preferably has sockets that are receptive of the supports.

In one embodiment, the filter material preferably includes ribs.

In one embodiment, at least some of the supports preferably have a generally rectangular cross section.

In one embodiment, the movable support preferably has a generally cylindrical or rounded cross section.

In one embodiment, a sheath is preferably provided, sized and shaped to fit over the filter basket to define a collapsed, storage position.

In one embodiment, the filter material preferably extends circumferentially about the guidewire longitudinal axis, preferably 200-270 degrees, and more preferably, about one hundred eighty degrees.

In one embodiment, at least one hub preferably has a hub periphery and a hub opening spaced inwardly of said hub periphery.

In one embodiment, the supports preferably attach to the hub in between the hub opening and the hub periphery.

In one embodiment, there are preferably multiple sockets in between the hub opening and the hub periphery and the fixed supports preferably attach to the hub at the hub sockets.

The present invention provides in one embodiment, an aortic embolic filter apparatus, including an elongated catheter preferably having a length, proximal and distal end portions and a catheter lumen with a catheter central, longitudinal axis.

A catheter hub is preferably mounted on the catheter.

A tip hub is preferably spaced distally of the catheter hub.

A filter basket is preferably attached to the hubs and positioned distally of the catheter hub and proximally of the tip hub.

The filter basket preferably includes a supporting structure, such as multiple filter supports that each span from the catheter hub to the tip hub.

A filter material is preferably supported by the filter supports.

The filter basket preferably has concave and convex surfaces, first and second edge portions, and a filter basket opening that preferably spans most of the distance between the hubs and in between the filter material first and second edge portions.

One of the supports is preferably a movable support that is longitudinally movable relative to the catheter hub wherein the movable support slides relative to the catheter hub; and an operator, controller or handle enables the movable support to change length between the hubs to put more or less of a curvature to the filter basket.

In one embodiment, the fixed supports preferably have one or more curved sections.

In one embodiment, there are preferably three fixed supports.

In one embodiment, the movable support preferably extends the full length of the catheter.

In one embodiment, the apparatus preferably includes a guidewire, each of the hubs having a hub opening, and the guidewire extends through the hub openings and catheter lumen.

In one embodiment, a handle is preferably attached to the proximal end portion of the catheter, the handle including a controller that enables movement of the movable support relative to the catheter hub.

In one embodiment, the controller preferably includes a rotatable member and wherein the movable support is preferably wound upon the rotatable member.

In one embodiment, each hub preferably has sockets that are receptive of the supports.

In one embodiment, the filter material preferably includes transversely placed ribs.

In one embodiment, at least some of the supports preferably have a generally cross section that is not circular.

In one embodiment, the movable support preferably has a generally rounded cross section.

In one embodiment, a sheath is provided that is preferably sized and shaped to fit over the filter basket to define a collapsed storage position wherein the filter basket is inside the sheath.

In one embodiment, the filter material preferably extends circumferentially about the catheter central longitudinal axis less than 360 degrees.

In one embodiment, at least one hub preferably has a hub periphery and a hub opening spaced inwardly of said hub periphery.

In one embodiment, multiple of the supports preferably attach to the hub in between the hub opening and the hub periphery.

In one embodiment, there are multiple sockets next to the hub opening and the fixed supports attach to the hub at the hub sockets.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
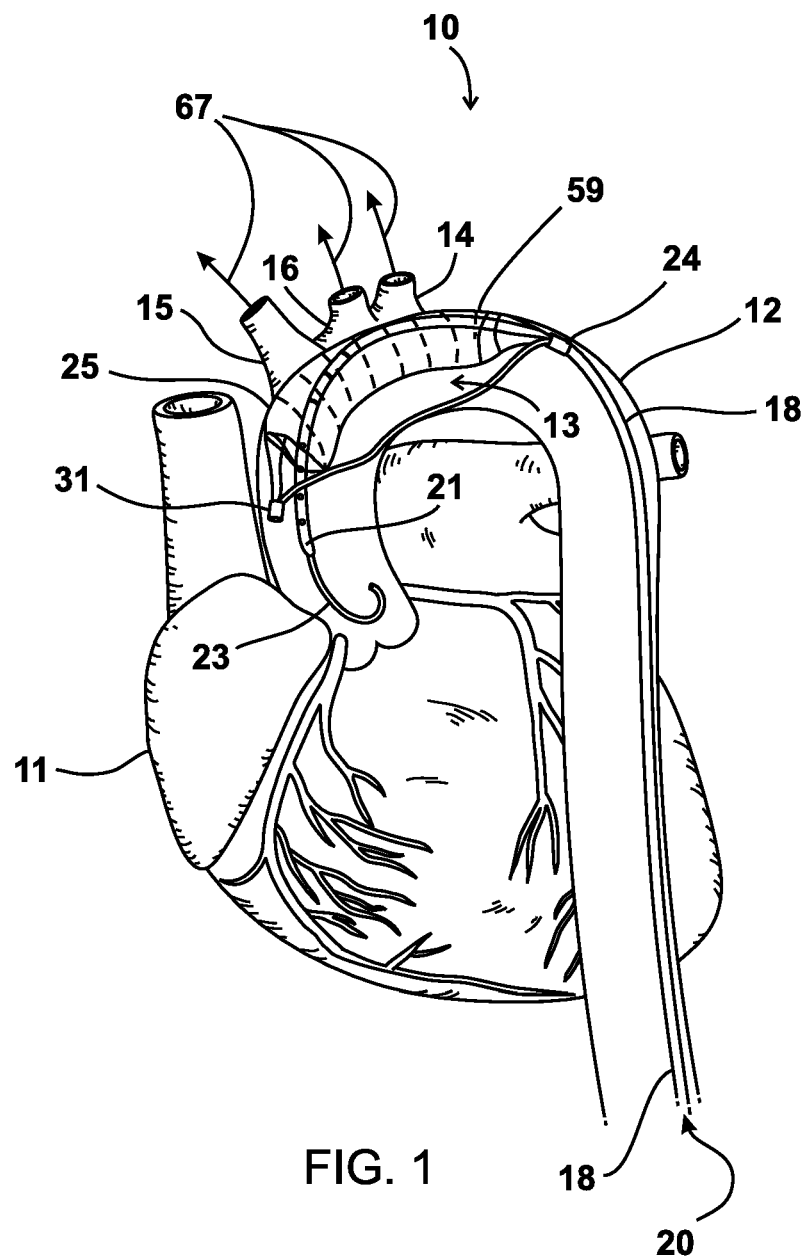
FIG. 1 is a schematic diagram of a preferred embodiment of the apparatus of the present invention showing deployment in a patient's aorta with sheath, catheter, filter basket and guidewire in operative positions.

FIG. 1 is a perspective view showing the apparatus 10 of the present invention after placement in a patient's heart 11, and more particularly in annulus 13 of aorta 12. A plurality of arteries 14, 15, 16 are shown discharging blood (indicated by arrows 67) from aorta 12. These arteries 14-16 include the brachiocephalic artery, carotid artery and left subclavian artery.

Figure 11:
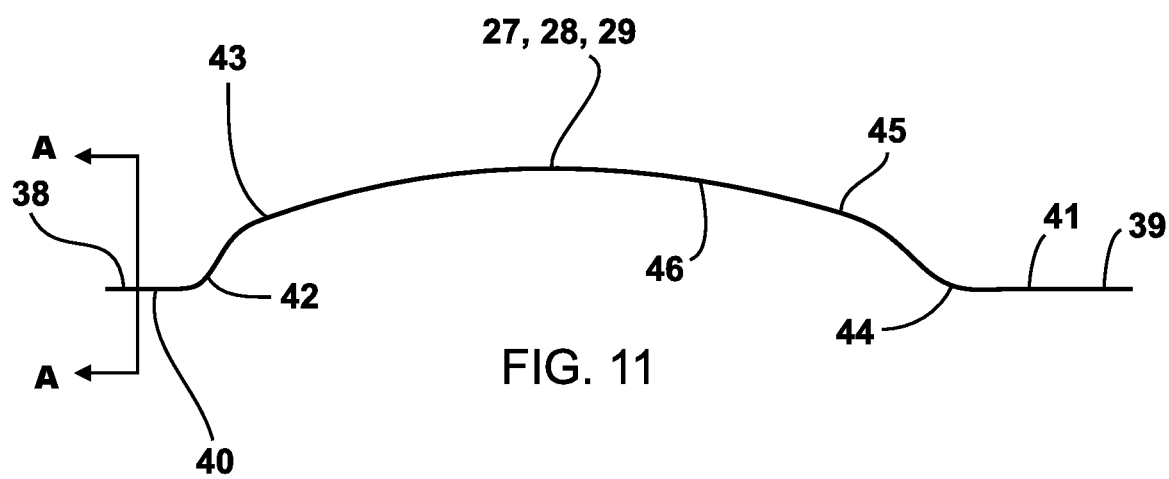
FIG. 11 is a partial perspective view of a fixed basket support member of a preferred embodiment of the apparatus of the present invention.
Figure 12:
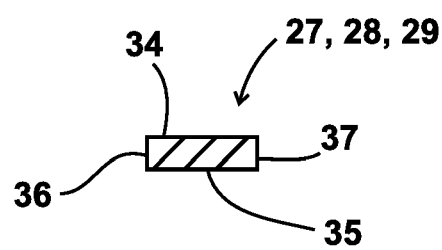
FIG. 12 is a sectional view taken along lines A-A of FIG. 11.

Embolic protection basket/catheter apparatus 10 includes catheter shaft 18 or polymeric tube having a catheter lumen 20. A distal end portion of catheter shaft 18 is connected to fitting or catheter hub or sprocket 24. Basket or filter 25 occupies a position in between fitting or catheter hub or sprocket 24 and distally located tip hub, hub, or fitting or tip 31. A plurality of supports spans between the fittings or hubs 24 and 31 (see FIGS. 1 and 5-10). These supports include a plurality of fixed supports 27, 28, 29 and an adjustable or movable support or arm 30. The fixed supports 27, 28, 29 can be seen in more detail in FIGS. 11-12. The movable or adjustable support 30 can be seen in more detail in FIGS. 13-14. Each of the fixed supports 27, 28, 29 can be of the same size and shape as shown in FIGS. 11-12. Each support 27, 28, 29 has ends or end portions 38, 39. End portion 38 has straight section 40 that connects with bend 42. Bend 42 connects with bend 43. End portion 39 has straight section 41 that connects with bend 44. Bend 44 connects with bend 45. Arch section 46 connects with bends 43, 45 as seen in FIG. 11. The cross section A-A of FIG. 11 is shown as FIG. 12. In FIG. 12, each support 27, 28, 29 has flat surfaces 34, 35 and edge surfaces 36, 37.

Figure 13:
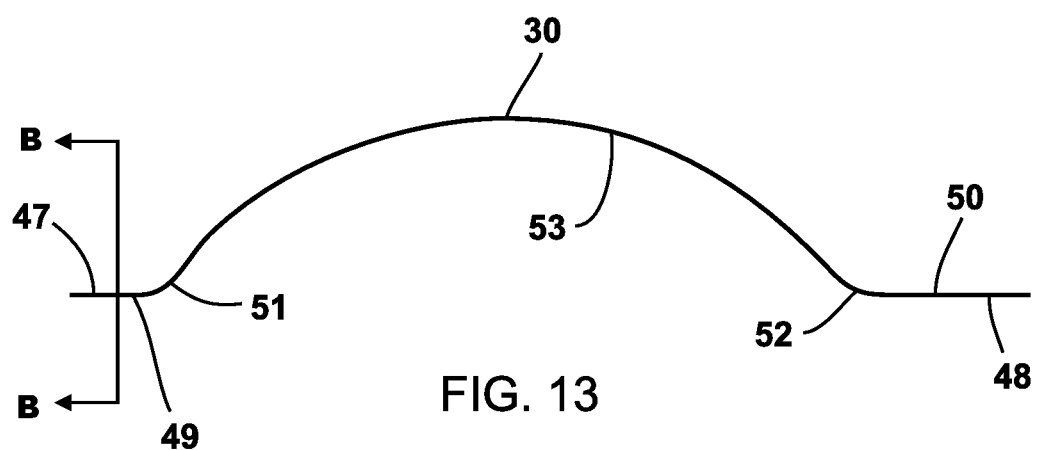
FIG. 13 is a partial perspective view of a movable basket support member of a preferred embodiment of the apparatus of the present invention.
Figure 14:
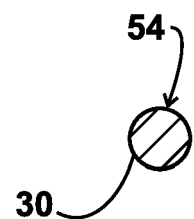
FIG. 14 is a sectional view taken along lines B-B of FIG. 13.

FIGS. 13-14 show the movable or adjustable support 30 in more detail. Support 30 has end portions 47, 48. Each end portion 47, 48 can have a straight section 49 or 50 in FIG. 13. Arch section 53 connects with bends 51, 52. Bend 51 connects with straight section 49. Bend 52 connects with straight section 50. Movable support 30 can have a generally cylindrical or circular cross section with outer surface 54 as shown in FIG. 14.

A sheet or expanse of filter material 26 is attached to the fixed supports 27, 28, 29 as seen in FIGS. 2-3 and 5-10. The configuration of sheet of material 26 can be changed by applying more or less tension to adjustable support 30. The movable or adjustable support 30 is fixedly attached to tip hub or distal tip fitting 31. A slidable connection is provided at fitting or sprocket or catheter hub 24 with adjustable support 30. The basket/catheter apparatus 10 has a basket or filter 25 at the distal end 56, a controller or handle 60 at the proximal end 55, and a flexible polymeric catheter or catheter shaft 18 connecting the two ends. The controller or handle 60 has a flush port 65 on top that allows for flushing the catheter lumen 20 with e.g., saline, heparin, contrast or other media. The controller/handle 60 has a guidewire/pigtail port 64 that allows for the guidewire/pigtail 23, 21 changes. Once the orientation of the filter or basket 25 position is achieved, rotating tension knob 62 on controller or handle 60 body 61 (see FIG. 4) increases the movable/adjustable support arm 30 tension. This increased tension on the movable/adjustable support arm 30 will help in keeping the filter/basket 25 in a curved position (e.g. see FIG. 1) during the procedure. For instance, increasing the tension on the adjustable/movable support arm 30 causes the filter/basket 25 to form an arc or curve that closely matches the aortic arch curve as seen in FIG. 1. A pigtail catheter 21 having lumen 22 can be advanced over the guidewire 23 wherein the guidewire 23 occupies the lumen 22. The pigtail catheter 21 is then placed in the left ventricular outflow tract (LVOT) or wherever desired.

The basket/catheter apparatus 10 has basket/filter 25 at a distal end portion 56, a controller or handle 60 at the proximal end portion 55, and a flexible polymeric catheter shaft 18 connecting to handle/controller 60 and to catheter hub, sprocket or fitting 24.

The basket/filter 25 can be constructed out of a plurality of shape-set supports or ribbons (see FIGS. 11-12) 27, 28, 29 (e.g., nitinol) and a movable or adjustable support, arm, or wire 30 (see FIGS. 13-14). The basket/filter 25 can have at least four of the ribbons, wires, arms or supports 27, 28, 29, 30. Three supports or arms 27, 28, 29 are fixed at both ends. One of the supports or arms 30 is fixed only at the distal end to fitting, hub or tip 31, and sliding at its other end relative to sprocket, catheter hub, fitting 24 allowing for basket/filter 25 size adjustments appropriately to the anatomy/procedure. Alternatively, the basket/filter 25 can be milled from e.g., a tube of nitinol and then covered with a sheet of filter material 26, 32 (see FIGS. 2, 3).

The fixed nitinol supports or arms 27, 28, 29 (see FIGS. 11, 12) are shape-set in the configuration out of preferably 0.002-0.010 inches (0.005-0.025 cm) by 0.010-0.060 inches (0.025-0.152 cm), more preferably, 0.003-0.007 inches (0.008-0.018 cm) by 0.030-0.050 inches (0.076-0.127 cm), and most preferably 0.005 inches by 0.020 inches (0.0127 cm by 0.0508 cm), nitinol support or ribbon (see FIGS. 11-12). The adjustable support or arm 30 (see FIGS. 5-10, 13, 14) is fixed only at the distal end to tip or fitting or hub 31 and is shape-set out of, for example, preferably 0.005-0.040 inch (0.013-0.102 cm) wire, more preferably 0.010-0.030 inch (0.025-0.076 cm) wire, and most preferably 0.020 inch (0.0508 cm) wire. All four supports or arms 27, 28, 29, 30 are fixedly secured at the distal end portion 56 to fitting, hub or tip 31 which can be made out of either polymeric material or metal. The nitinol supports or arms 27, 28, 29, 30 can be secured to the fitting, tip hub or tip 31 at sockets 71, 72, 73, 74 either by e.g., adhesive, welding, soldering or crimping. Each hub or fitting 24, 31 has a through hole in the middle for guidewire 23 of preferably 0.009-0.045 inches (0.023-0.114 cm) in diameter, more preferably 0.014-0.035 inches (0.0356-0.089 cm) in diameter, and most preferably 0.035 inches (0.0889 cm) in diameter to pass through for the initial placement of the basket/filter 25 in the patient's aorta 12.

A filter material or sheet of filter material 32 is secured to the three fixed filter supporting arms 27, 28, 29 by sewing, adhesives or by heat-sealing to itself. The filter material 32 can be made out of e.g., nylon fabric with thickness of preferably 5-200 µm, more preferably 25-150 µm, and most preferably for example around 84 µm and having mesh opening of preferably 10-200 µm, more preferably 50-175 µm, and most preferably 140 µm. The nitinol arms or supports 27, 28, 29, 30 are assembled with the filter material 32 to form a minimum deployed diameter of for example about 0.75 inches (1.905 cm). At the proximal end of the basket/filter 25, the arms 27, 28, 29, 30 are assembled using a hub, fitting or sprocket 24 with two exceptions: 1) at the catheter hub 24, the through hole 57 is large enough for a pigtail catheter to pass through; and 2) the movable or adjustable supporting arm 30 attaches to a securement hole 58 that is large enough for the arm 30 to slide freely relative to the catheter hub 24.

Figures 16, 17:
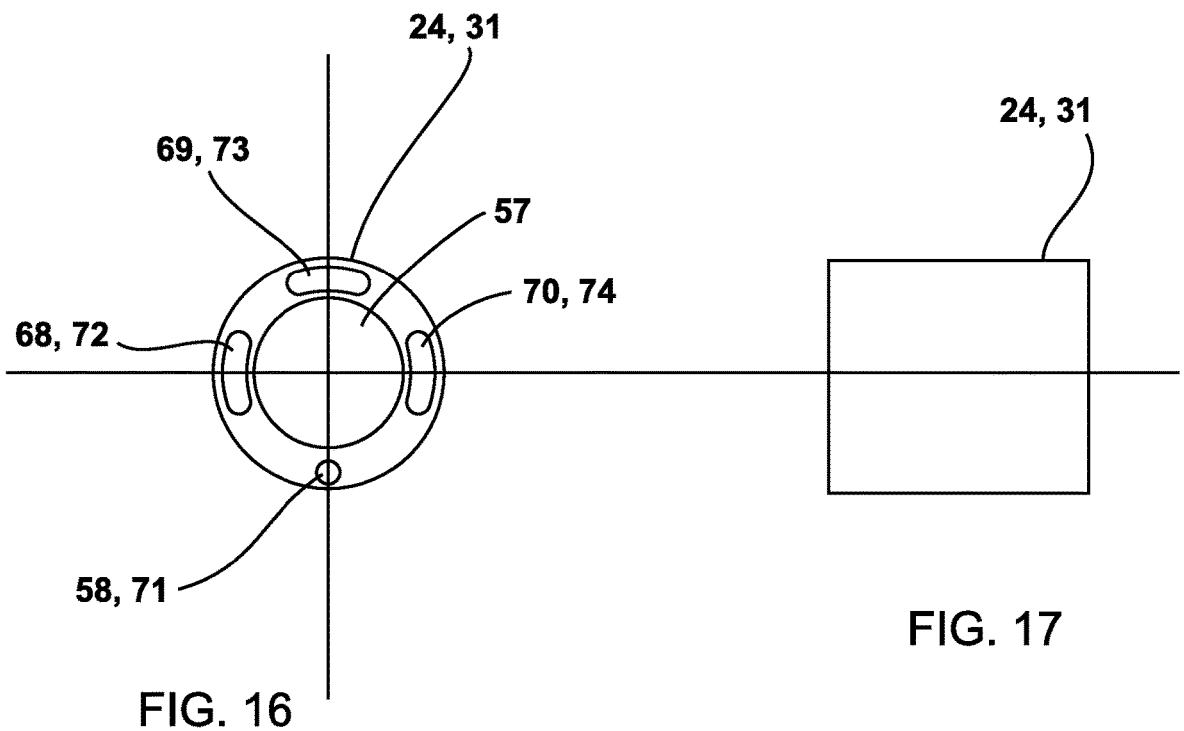
FIG. 16 is an end view of the hub of FIG. 15.
FIG. 17 is a side view of the hub of FIG. 15.
Figure 15:
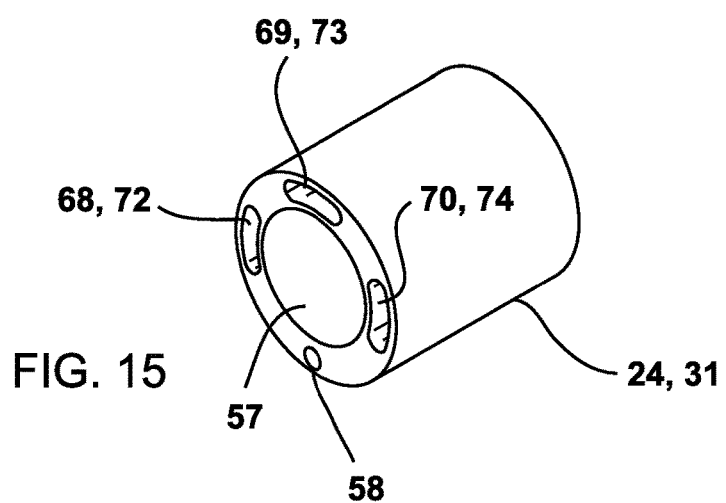
FIG. 15 is a fragmentary perspective view showing a hub of a preferred embodiment of the apparatus of the present invention.

The fixed filter supporting arms 27, 28, 29 are secured at the proximal end or catheter hub 24 in similar fashion as at the tip hub 31, and these three arms 27, 28, 29 are terminated at this junction with catheter hub 24. The movable or adjustable supporting arm 30 is passed through the sprocket 24 opening 58 and terminated in the controller or handle 60 of the catheter 18. In FIGS. 15-17, there can be seen hubs 24, 31. Hubs 24, 31 can also be referred to as fittings or sprockets. Hubs 24, 31 can be similarly sized and shaped. Hub 31 is a distal or tip hub to which all supports 27, 28, 29, 30 are attached. In that regard, each hub 31 has sockets 68, 69, 70 that form a connection with end portions 38 of supports 27, 28, 29. Hub 31 has a cylindrical or rounded socket 71 that forms a connection with end portion 47 of movable support 30. Each of the supports 27, 28, 29, 30 is affixed or attached to tip or hub 31 using adhesive, welding soldering or crimping.

Only supports 27, 28, 29 are rigidly or fixedly attached to hub 24 (using e.g., adhesive, welding, soldering or crimping). Hub 24 has an opening at 58 that is large enough for movable support 30 to slide at opening 58 relative to hub 24. Hub 24 has central opening 57 that enables passage of guidewire 23 and pigtail catheter 21.

In order to better secure the filter material 32 and to make it collapse easily, small diameter wires 33 can be weaved through the filter material 32 like ribs. The ends of the ribs/wires 33 can be secured to the fixed filter supporting arms 27, 28, 29 using e.g., adhesive, solder or welds. Superelastic nitinol wires can be used for ribs 33, each preferably 0.001-0.010 inches (0.00254-0.0254 cm) in diameter, more preferably 0.002-0.008 inches (0.00508-0.02032 cm) in diameter, and most preferably about 0.003 inches (0.00762 cm) in diameter. The number and spacing of ribs 33 can vary. Typical spacing between the ribs 33 can be preferably 0.050-0.500 inches (0.127-1.270 cm), more preferably 0.100-0.300 inches (0.254-0.762 cm), and most preferably about 0.200 inches (0.508 cm).

Figure 18:
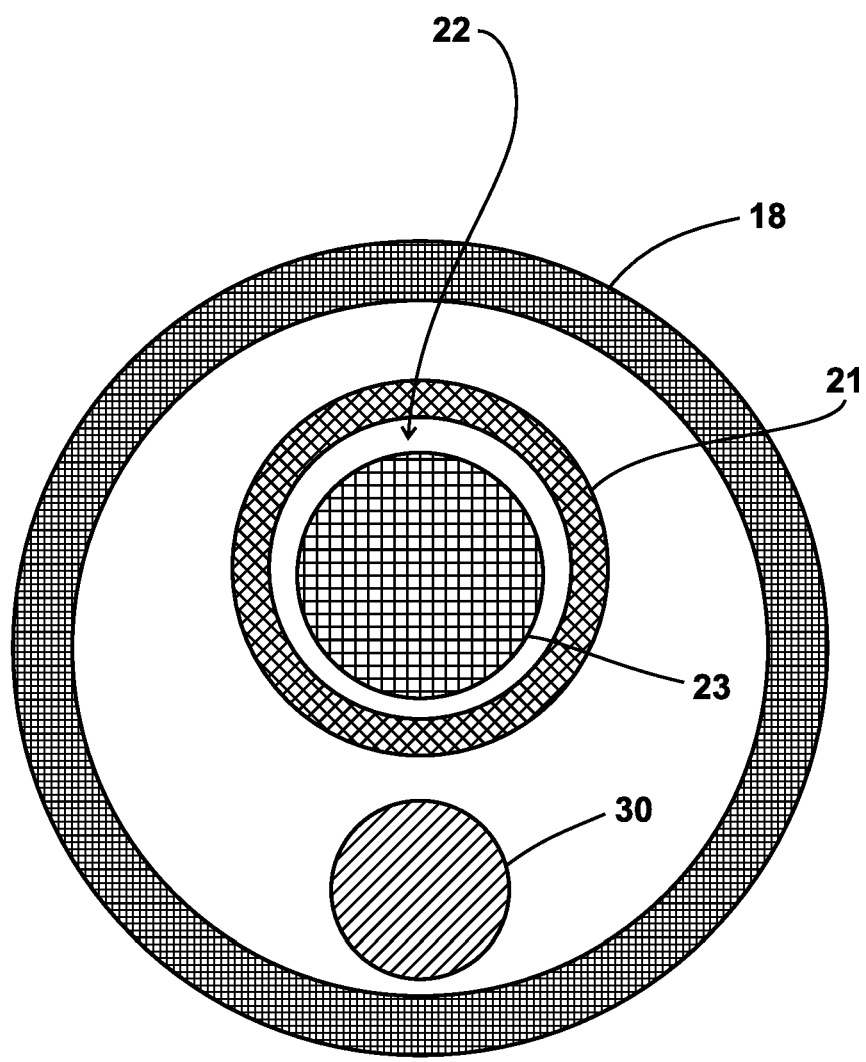
FIG. 18 is a partial sectional view of a preferred embodiment of the apparatus of the present invention.

The basket/filter 25 can be secured to a catheter polymeric shaft 18 either by heat fusing or by adhesives. A cross sectional view of the catheter assembly is shown in FIG. 18.

The catheter shaft 18 can be e.g., an extruded polymeric tube having a bore or lumen 20. The polymeric shaft 18 could be reinforced with e.g., metal braids, monofilament or yarn to improve column strength and to improve kink resistance. Polymeric material can be used for the shaft 18 and can be e.g., Pebax, Nylon, PVDF (Polyvinylidene Fluoride) or Polyurethane.

Figure 2:
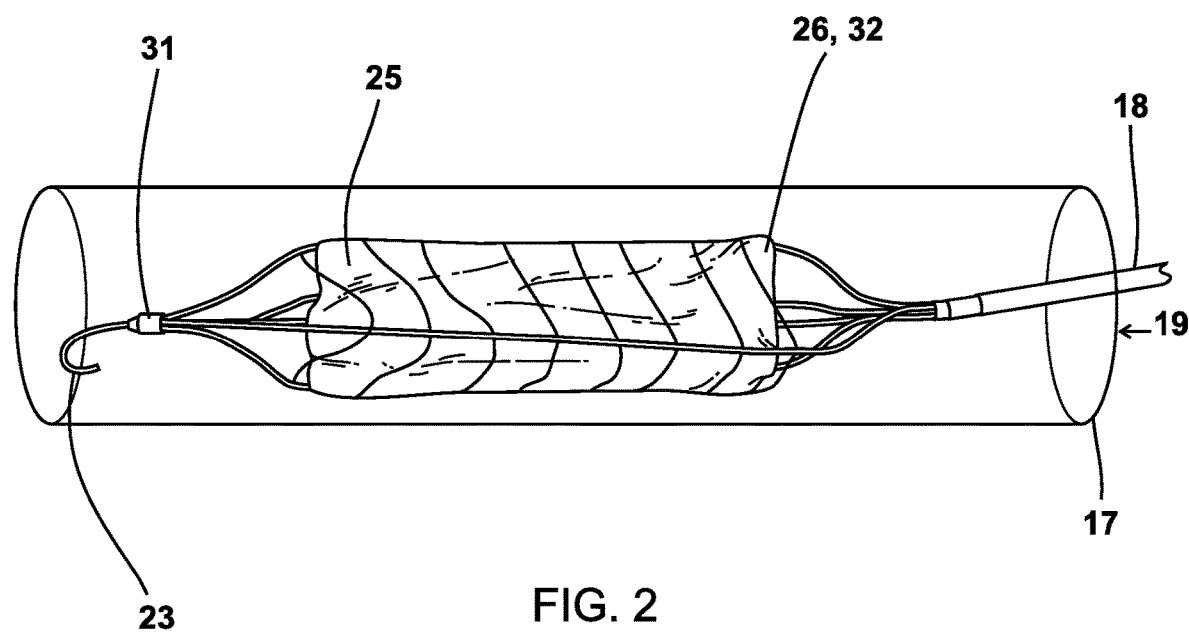
FIG. 2 is a side view of a preferred embodiment of the apparatus of the present invention.
Figure 3:
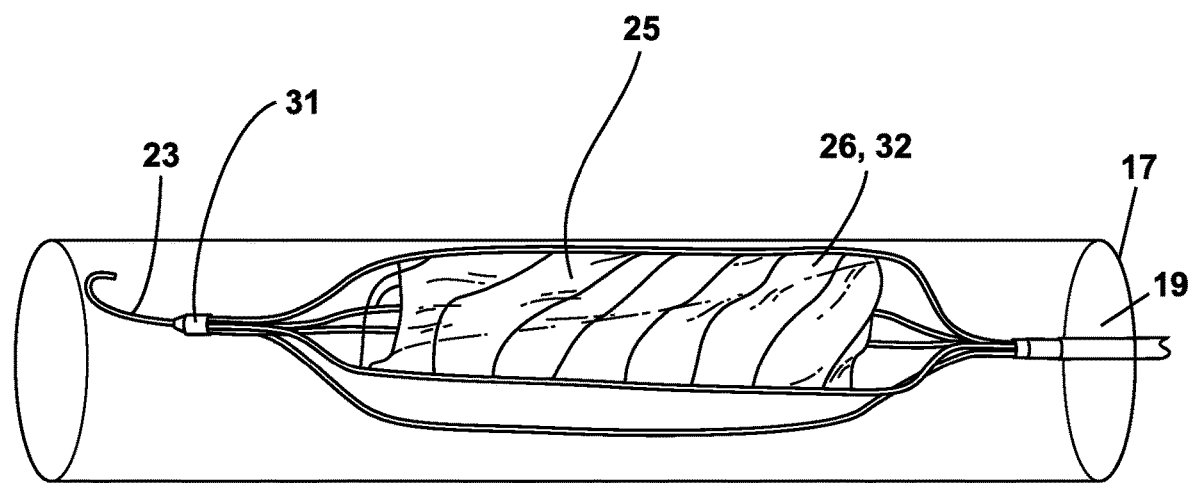
FIG. 3 is a side view of a preferred embodiment of the apparatus of the present invention.

The catheter shaft 18 connects to controller or handle 60 at the proximal end via a connector/strain relief 66. The catheter shaft 18 connects to the catheter hub 24 using UV curable adhesive, Cyanoacrylate adhesive or insert molding. The controller or handle 60 has a slider 63 on top for deploying and collapsing the basket/filter 25. A sheath 17 can be used to deploy the filter/basket 25. Sheath 17 initially holds basket/filter 25 in sheath lumen 19 as seen in FIGS. 2-3. Sheath 17 can be preferably a 5 F-16 F sheath and most preferably a 7 F or 10 F sheath. Sheath 17 is placed in the lumen 13 of a patient's aorta 12 over guidewire 23. Catheter 18 and basket/filter 25 are then introduced into the sheath 17 lumen 19 and over guidewire 23. The basket/filter 25 and catheter 21 are then tracked over guidewire 23 to the aortic arch region 59 (see FIG. 1) while viewing position under fluoroscopy.

Operator or slider 63 on handle or controller 60 body 61 deploys the filter/basket 25 pulling the sheath 17 to release and place the basket/filter 25 to the position in the aortic arch 59 seen in FIG. 1. Orientation of the filter/basket 25 position can be manipulated by rotating the catheter shaft 18 while the movable/adjustable support arm 30 is under minimal tension. Once the desired orientation of the filter/basket 25 is achieved, rotating knob 62 increases the movable support arm 30 tension. This increased tension on the movable support arm 30 keeps the filter/basket 25 in position during the procedure, filtering blood flow from the aorta 12 to the arteries 14, 15, 16 that discharge from the aorta 12 in the direction of arrows 67 (see FIG. 1).

Increasing the tension of the movable/adjustable support arm 30 enables a surgeon, technician or nurse to shape the filter/basket 25 to form an arc or curved shape that closely matches the aortic arch 59 curve. Pigtail catheter 21 having lumen 22 can be advanced over guidewire 23 (see FIGS. 1, 9-10 and 18). The pigtail catheter 21 can be then placed in the left ventricular outflow tract or other desired locale.

The present invention includes an aortic embolic filter apparatus 10, comprising: an elongated catheter 18; a pair of spaced apart hubs 24, 31; a filter basket 25 attached to the hubs 24, 31, wherein the filter basket 25 includes multiple supports 27, 28, 29, 30; and, a filter material 26 that is supported by the supports, wherein, one of the supports being a support that is movable 30 relative to the catheter hub 24, and wherein an operator 63 handle or controller 60 body 61 enables the movable support 30 to change length between the hubs 24, 31 to put more or less of a curvature of the filter basket 25.

In one embodiment, the fixed supports 27, 28, 29 are curved as shown in FIG. 11.

In one embodiment, there are at least three fixed supports 27, 28, 29 as shown in FIGS. 5-10.

In one embodiment, the movable support 30 extends the full length of the catheter 18.

Figure 7:
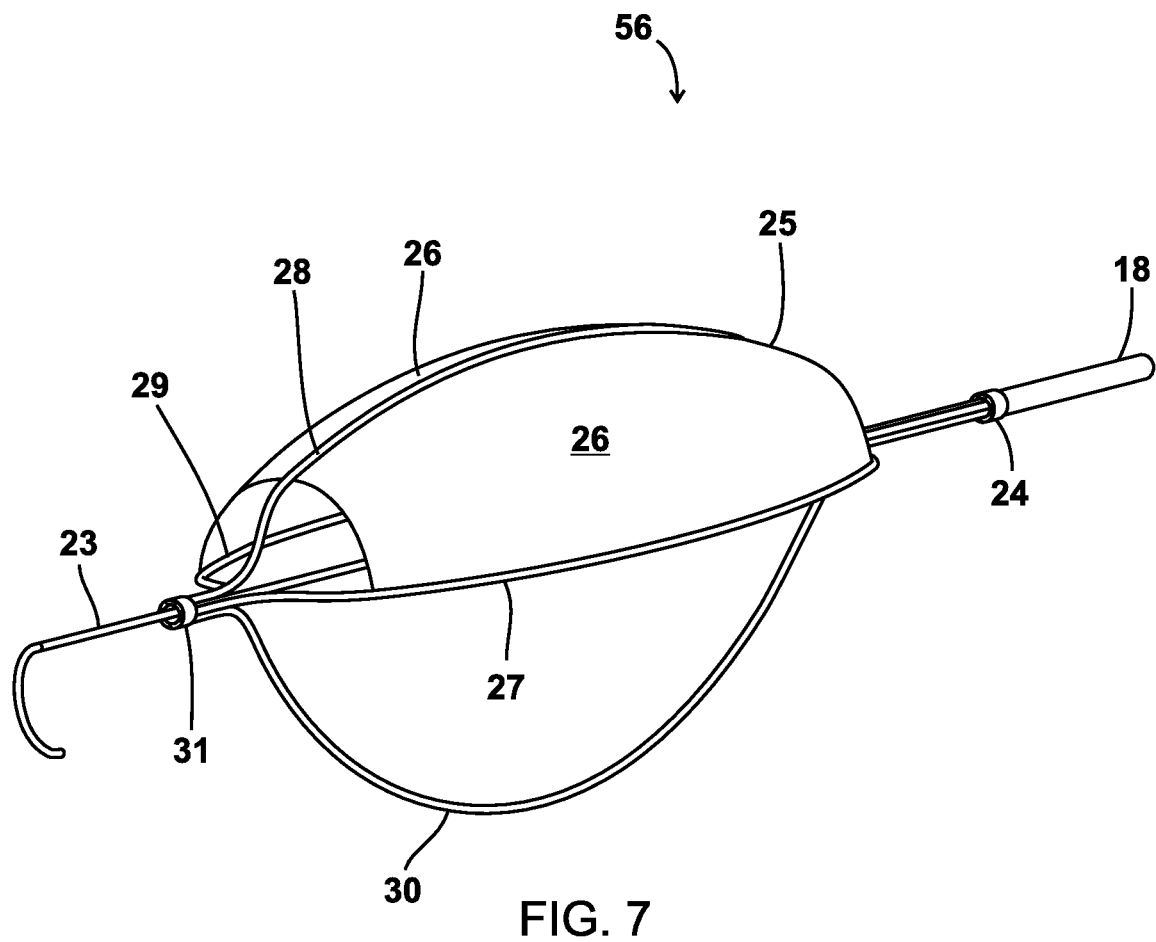
FIG. 7 is a partial perspective view of a preferred embodiment of the apparatus of the present invention.
Figure 8:
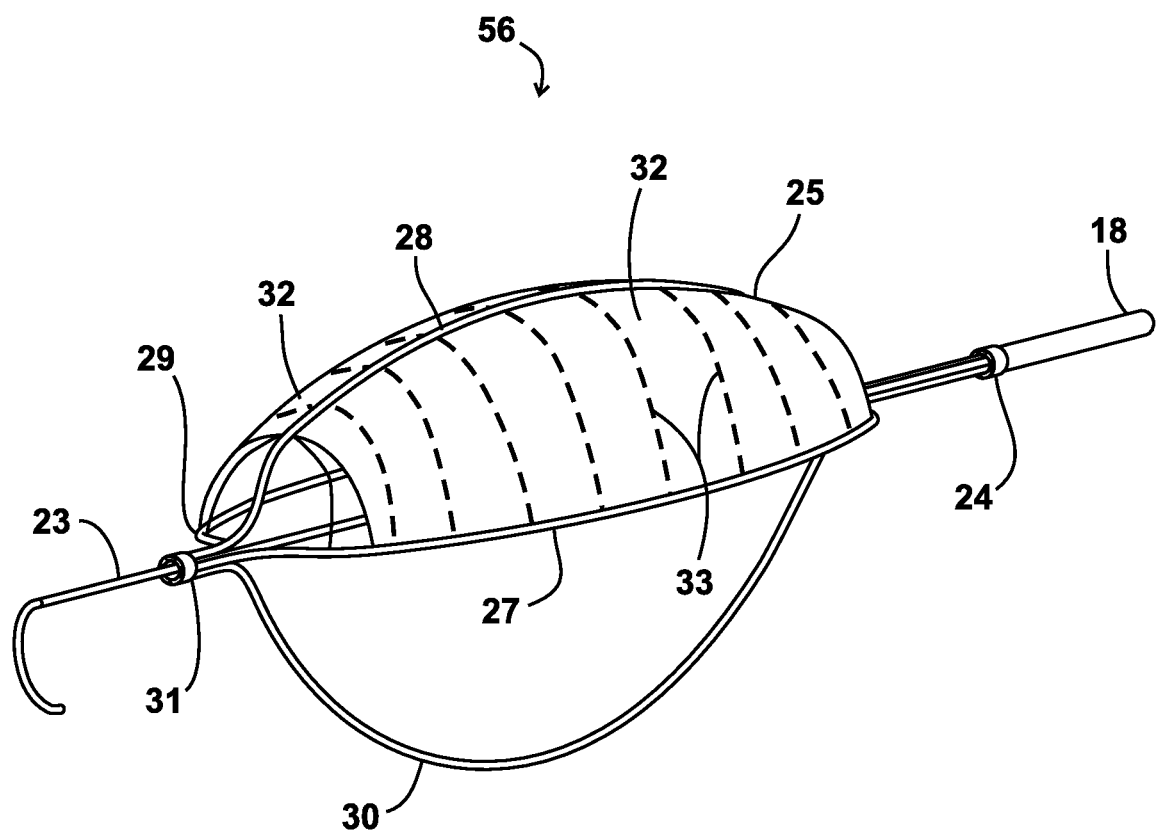
FIG. 8 is a partial perspective view of a preferred embodiment of the apparatus of the present invention and showing an alternate filter basket arrangement.
Figure 9:
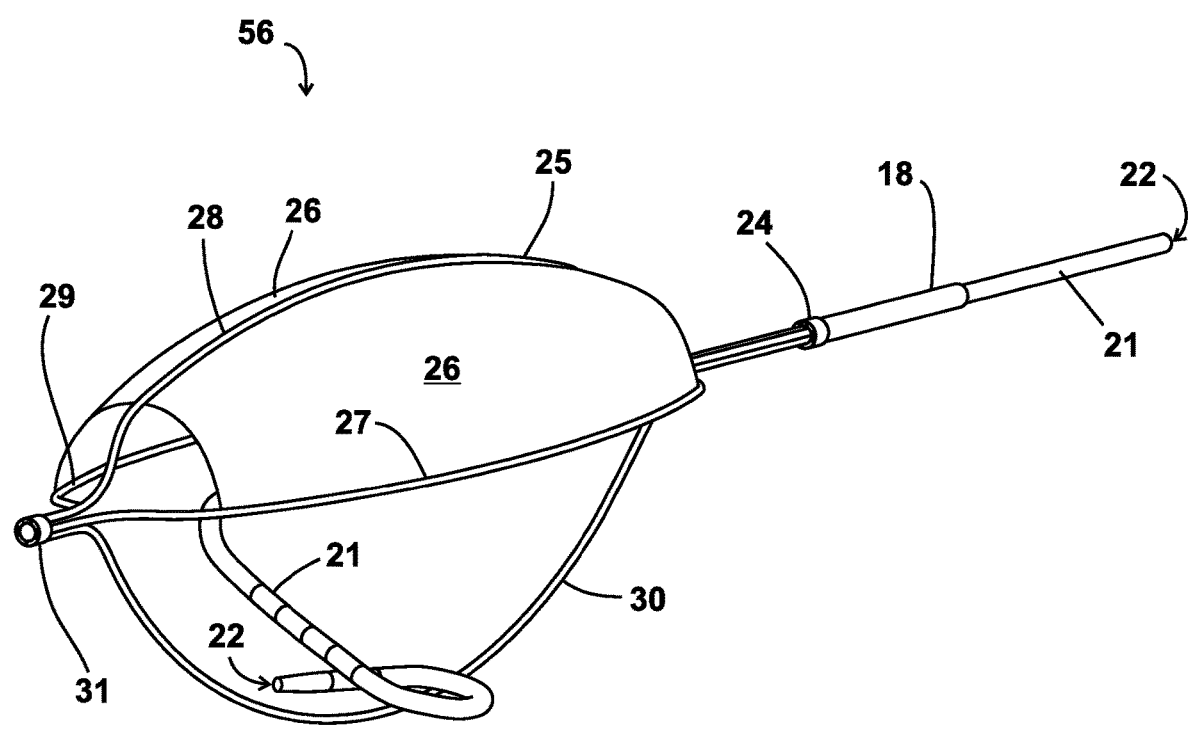
FIG. 9 is a partial perspective view of a preferred embodiment of the apparatus of the present invention.

In one embodiment, the apparatus 10 includes a guidewire 23 as shown in FIGS. 1, 7, and 8, and each of the hubs 24, 31 has a hub opening 57 and the guidewire 23 extending through the hub openings 57.

Figure 4:
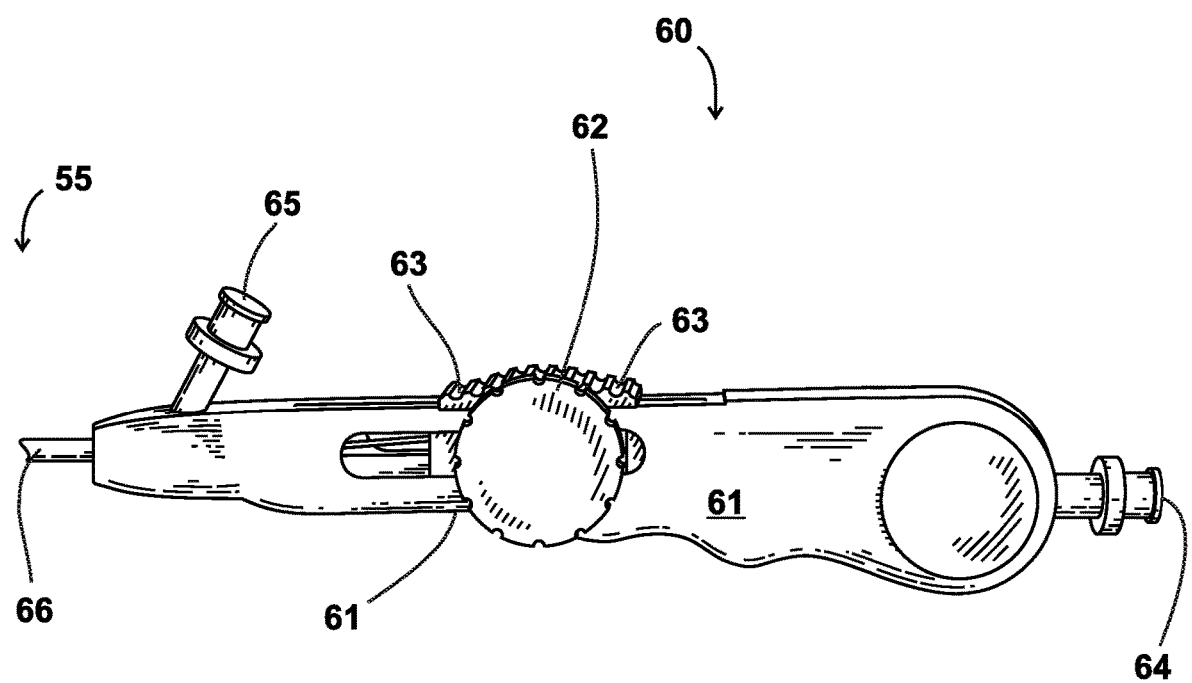
FIG. 4 is a side view of the handle/controller of a preferred embodiment of the apparatus of the present invention.
Figure 5:
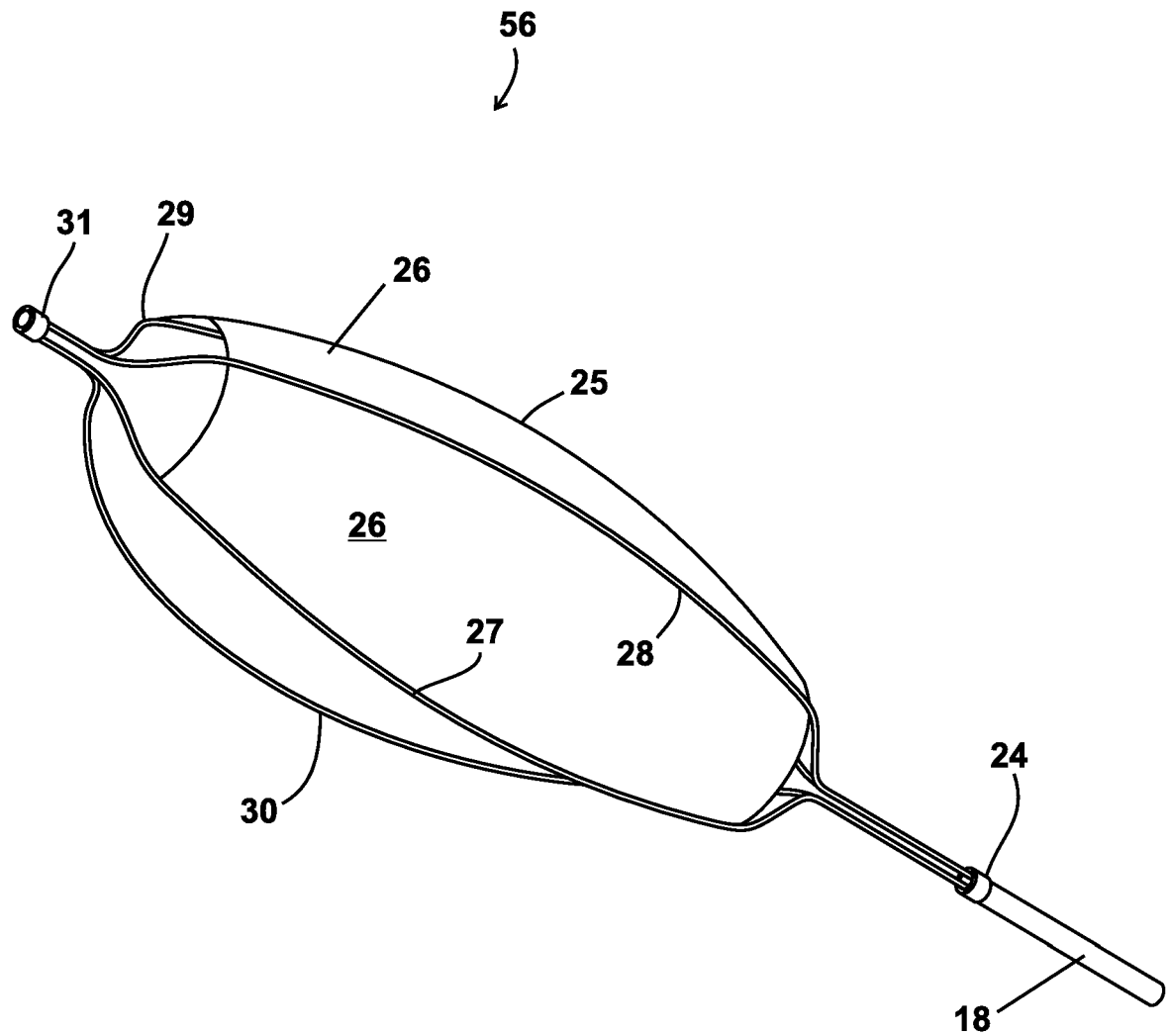
FIG. 5 is a partial perspective view of a preferred embodiment of the apparatus of the present invention.

In one embodiment, the filter apparatus 10 further comprises a controller 60 attached to the proximal end portion 55 of the catheter 18, the controller 60 including an actuator 63 that moves the movable support 30. In another embodiment, the controller 60 includes a rotatable knob 62 as shown in FIG. 4.

In one embodiment, each hub 24, 31 has sockets 68, 69, 70, 72, 73, 74 that are receptive of the supports 27, 28, 29.

Figure 6:
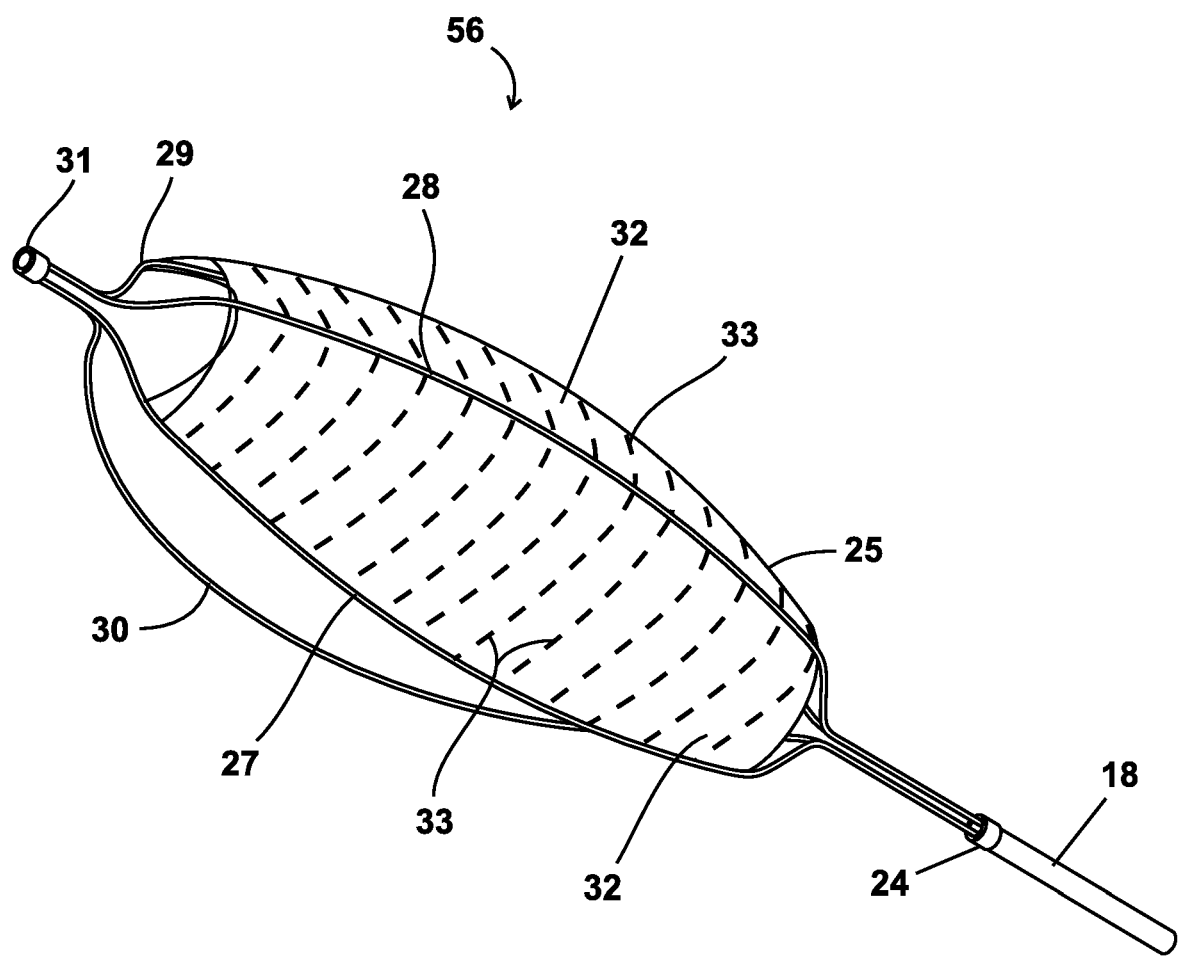
FIG. 6 is a partial perspective view of a preferred embodiment of the apparatus of the present invention and showing an alternate filter basket arrangement.
Figure 10:
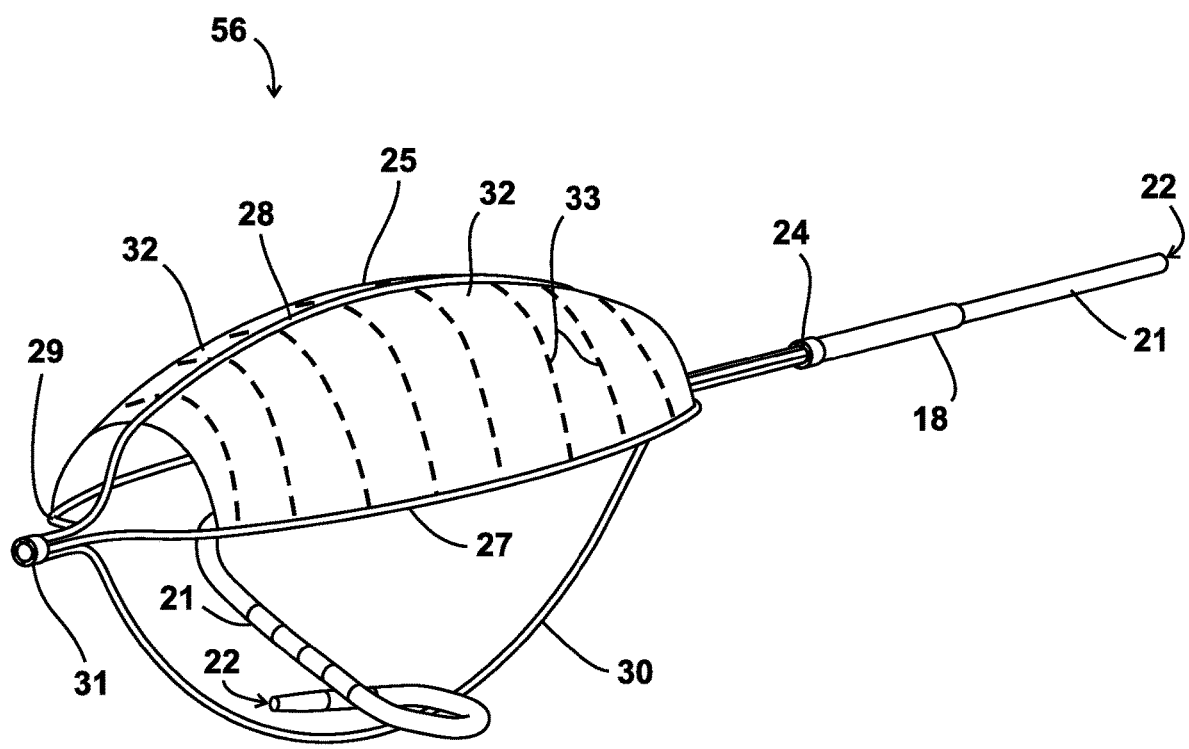
FIG. 10 is a partial perspective view of a preferred embodiment of the apparatus of the present invention and showing an alternate filter basket arrangement.

In one embodiment, the filter material 32 includes ribs 33 as shown in FIGS. 6, 8, and 10.

In one embodiment, at least some of the supports 27, 28, 29 for the filter material 26, 32 have a generally rectangular cross section as shown in FIG. 12.

In one embodiment, the movable support 30 has a generally cylindrical cross section as shown in FIG. 14.

In one embodiment, the filter apparatus 10 further comprises a sheath 19 sized and shaped to fit over the filter basket 25 to define a collapsed storage position as shown in FIGS. 2-3.

In one embodiment, the filter material 26, 32 extends circumferentially about the catheter 18 central longitudinal axis about one hundred eighty degrees.

In one embodiment, at least one hub 24, 31 has a hub periphery and a hub opening 57 spaced inwardly of said hub periphery. In this embodiment, the supports 27, 28, 29, 30 attach to the hub 24, 31 in between the hub opening 57 and the hub periphery. Additionally, there may be multiple sockets 68, 69, 70, 72, 73, 74 in between the hub opening 57 and the hub periphery and the fixed supports 27, 28, 29 attach to the hub 24, 31 at the hub sockets 68, 69, 70, 72, 73, 74.

The present invention also includes an aortic embolic filter apparatus 10, comprising: an elongated catheter 18; a catheter hub 24 mounted on the catheter 18; a tip hub 31 spaced distally of the catheter hub 24; a filter basket 25 attached to the hubs 24, 31 and positioned distally of the catheter hub 24 and proximally of the tip hub 31, the filter basket 25 including multiple filter supports 27, 28, 29, 30 that each span from the catheter hub 24 to the tip hub 31; a filter material 26, 32 that is supported by the filter supports 27, 28, 29, 30, wherein one of the supports is movable 30 relative to the catheter hub 24; and a controller 60 that enables the movable support 30 to change length between the hubs 24, 31 to put more or less of a curvature to the filter basket 25.

In one embodiment, the fixed supports 27, 28, 29 have one or more curved sections 42, 43, 44, 45, 46 as shown in FIG. 11.

In one embodiment, there are three fixed supports 27, 28, 29 as shown in FIGS. 5-10.

In one embodiment, the movable support 30 extends the full length of the catheter 18.

In one embodiment, the apparatus 10 includes a guidewire 23, each of the hubs 24, 31 having a hub opening 57 and the guidewire 23 extends through the hub openings 57 and catheter lumen 20 as shown in FIGS. 1 and 18.

In one embodiment, the filter apparatus 10 further comprises a controller 60 attached to the proximal end portion 55 of the catheter 18, the controller 60 including a slider 63 that enables movement of the movable support 30 relative to the catheter hub 24. In this embodiment, the controller may include a rotatable member 62 and wherein the movable support 30 is wound upon the rotatable member 62.

In one embodiment, each hub 24, 31 has openings or sockets 58, 68, 69, 70, 71, 72, 73, 74 that are receptive of the supports 27, 28, 29, 30 as shown in FIGS. 15 and 16.

In one embodiment, the filter material 32 includes transversely placed ribs 33 as shown in FIGS. 6, 8, and 10.

In one embodiment, at least some of the supports 27, 28, 29 have a generally cross section that is not circular as shown in FIG. 12.

In one embodiment, the movable support 30 has a generally rounded cross section as shown in FIG. 14.

In one embodiment, the filter apparatus 10 further comprises a sheath 19 that is sized and shaped to fit over the filter basket 25 to define a collapsed storage position wherein the filter basket 25 is inside the sheath 19 as shown in FIGS. 2-3.

In one embodiment, the filter material 26, 32 extends circumferentially about the catheter 18 central longitudinal axis less than 360 degrees.

In one embodiment, at least one hub 24, 31 has a hub periphery and a hub opening 57 spaced inwardly of said hub periphery. In this embodiment, multiple of the supports 27, 28, 29, 30 attach to the hub 24, 31 in between the hub opening 57 and the hub periphery as shown in FIGS. 15-16.

The following is a list of parts and materials suitable for use in the present invention:

PARTS LIST

Part Number Description
- 10 embolic protection basket apparatus
- 11 patient's heart
- 12 patient's aorta
- 13 aorta annulus/lumen
- 14 artery
- 15 artery
- 16 artery
- 17 sheath
- 18 catheter/polymeric shaft
- 19 sheath lumen
- 20 catheter lumen
- 21 pigtail catheter
- 22 pigtail catheter lumen
- 23 guidewire
- 24 sprocket/fitting/catheter hub
- 25 filter/basket
- 26 filter material/sheet
- 27 fixed support/arm
- 28 fixed support/arm
- 29 fixed support/arm
- 30 movable support/arm/wire
- 31 tip/fitting/tip hub/hub
- 32 filter material/sheet of material
- 33 rib/wire
- 34 surface
- 35 surface
- 36 edge
- 37 edge
- 38 end portion
- 39 end portion
- 40 straight section
- 41 straight section
- 42 bend
- 43 bend
- 44 bend
- 45 bend
- 46 bend/curved section/arch section
- 47 end portion
- 48 end portion
- 49 straight section
- 50 straight section
- 51 bend
- 52 bend
- 53 bend/curved section/arch section
- 54 outer surface
- 55 proximal end portion
- 56 distal end portion
- 57 hole/opening
- 58 hole/opening
- 59 aortic arch region/aortic arch
- 60 controller/handle
- 61 body
- 62 knob/rotating member
- 63 slider/sliding member/actuator/operator
- 64 guidewire/pigtail catheter port
- 65 flush port
- 66 connector/strain relief/interface
- 67 arrow
- 68 socket
- 69 socket
- 70 socket
- 71 socket
- 72 socket
- 73 socket
- 74 socket All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:
1. An aortic embolic filter apparatus, comprising:
a) an elongated catheter having a length, proximal and distal end portions and a catheter lumen with a catheter central, longitudinal axis;
b) a pair of spaced apart hubs, at least one said hub being a catheter hub mounted on the catheter, the other hub being a tip hub attached to the catheter end spaced distally of the catheter hub;
c) a filter basket attached to the hubs and positioned distally of the catheter hub;
d) the filter basket including multiple fixed supports that each span from the catheter hub to the tip hub, each fixed support having first and second fixed support ends that are fixedly attached to said hubs wherein the first fixed end is attached to the catheter hub, and the second fixed end is attached to the tip hub;
e) a filter material that is supported by the fixed supports, said filter material having concave and convex surfaces, first and second edge portions, and an opening that spans most of the distance between the hubs and in between the filter material first and second edge portions;
f) wherein the catheter hub has an opening and further comprising a movable support that is longer than each fixed support and fixed to the tip hub and movable relative to the catheter hub, said movable support slidably mounted to the catheter hub at said opening, wherein said movable support is selectively movable to provide a curved portion that is spaced away from said catheter central, longitudinal axis;
g) said filter material spaced away from the movable support;
h) an operator that enables the movable support to change length between the hubs and to provide more or less of a curvature to the curved portion of the movable support and to the filter basket; and i) wherein the fixed supports do not change length between the hubs when the movable support changes length.

2. The aortic embolic filter apparatus of claim 1 wherein the supports are curved.

3. The aortic embolic filter apparatus of claim 1 wherein the movable support extends the full length of the catheter.

4. The aortic embolic filter apparatus of claim 1 wherein the apparatus includes a guidewire, each of the hubs having a hub opening and the guidewire extending through the hub openings.

5. The aortic embolic filter apparatus of claim 1 wherein each hub has sockets that are receptive of the fixed supports.

6. The aortic embolic filter apparatus of claim 1 wherein the catheter hub has a hub periphery and the hub opening of the catheter hub is spaced inwardly of the catheter hub periphery and wherein the supports attach to the catheter hub and in between the catheter hub opening and the catheter hub periphery, and wherein there are multiple sockets in between the catheter hub opening and the catheter hub periphery and the supports attach to the catheter hub at the hub sockets.

7. The aortic embolic filter apparatus of claim 1 wherein at least some of the supports have a generally rectangular cross section.

8. The aortic embolic filter apparatus of claim 1 wherein the movable support has a generally cylindrical cross section.

9. The aortic embolic filter apparatus of claim 1 further comprising a sheath that is sized and shaped to fit over and collapse the filter basket to define a filter storage position.

10. An aortic embolic filter apparatus, comprising:
a) an elongated catheter having a length, proximal and distal end portions and a catheter lumen with a catheter central, longitudinal axis;
b) a catheter hub mounted on the catheter, said catheter hub having a catheter hub opening;
c) a tip hub spaced distally of the catheter hub;
d) a filter basket attached to the hubs and positioned distally of the catheter hub and proximally of the tip hub;
e) the filter basket including a support structure that spans from the catheter hub to the tip hub;
f) a filter material that is supported by the support structure;
g) the filter basket having concave and convex surfaces, first and second edge portions, and a filter basket opening that spans most of the distance between the hubs and in between the filter material first and second edge portions;
h) a movable support that is fixed to the tip hub and longitudinally movable relative to the catheter hub wherein the catheter hub has a movable support opening and the movable support slides in said opening and relative to the catheter hub, wherein said movable support is selectively movable to provide a curved portion that is spaced away from said catheter central, longitudinal axis; and
i) an actuator that enables the movable support to change length between the hubs to put more or less of a curvature to the curved portion of the movable support and to the filter basket.

11. The aortic embolic filter apparatus of claim 10 wherein the movable support extends the full length of the catheter.

12. The aortic embolic filter apparatus of claim 10 wherein the actuator includes a controller that enables movement of the movable support relative to the catheter hub.

13. The aortic embolic filter apparatus of claim 10 wherein the movable support has a generally rounded cross section.

14. The aortic embolic filter apparatus of claim 10 wherein the filter material extends circumferentially about the catheter central longitudinal axis less than 360 degrees.

15. The aortic embolic filter apparatus of claim 10 wherein at least one hub has a hub periphery and a hub opening spaced inwardly of said hub periphery.

16. An aortic embolic filter apparatus, comprising:
a) an elongated catheter having a length, proximal and distal end portions and a catheter lumen with a catheter central, longitudinal axis;
b) a pair of spaced apart hubs, at least one said hub being a catheter hub mounted on the catheter, the other hub being a tip hub spaced distally of the catheter hub;
c) a filter basket attached to the hubs and positioned distally of the catheter hub;
d) the filter basket including multiple fixed supports that each span from the catheter hub to the tip hub, each fixed support having first and second fixed support ends that are fixedly attached to said hubs wherein the first fixed end is attached to the catheter hub, and the second fixed end is attached to the tip hub;
e) a filter material that is supported by the fixed supports, said filter material having concave and convex surfaces, first and second edge portions, and an opening that spans most of the distance between the hubs and in between the filter material first and second edge portions;
f) a movable support being a support that is fixed to the tip hub and slidable relative to the catheter hub, wherein said movable support is selectively movable to provide a curved portion that is spaced away from said catheter central, longitudinal axis; and
g) an operator that enables the movable support to change length between the hubs to change the curvature of the filter basket.

17. The aortic embolic filter apparatus of claim 16 wherein the movable support extends the full length of the catheter.

18. The aortic embolic filter apparatus of claim 16 wherein the apparatus includes a guidewire, each of the hubs having a hub opening and the guidewire extending through the hub openings.

19. The aortic embolic filter apparatus of claim 16 wherein at least one hub has a hub periphery and a hub opening spaced inwardly of said hub periphery.

20. The aortic embolic filter apparatus of claim 16 wherein the supports attach to the hub and in between the hub opening and the hub periphery, and wherein there are multiple sockets in between the hub opening and the hub periphery and the supports attach to the hub at the hub sockets.

* * * * *